United States Patent [19]

Ibbotson

[11] 4,031,026

[45] June 21, 1977

[54] DIPHENYLMETHANE DIISOCYANATE COMPOSITIONS

[75] Inventor: Arthur Ibbotson, Manchester, England

[73] Assignee: Imperial Chemical Industries Limited, London, England

[22] Filed: May 10, 1976

[21] Appl. No.: 684,963

[30] Foreign Application Priority Data

May 19, 1975 United Kingdom ............ 21293/75

[52] U.S. Cl. ...................... 252/182; 260/77.5 AT; 260/453 AM
[51] Int. Cl.² ........................................ C07C 119/48
[58] Field of Search ............... 252/182; 260/2.5 BF, 260/77.5 AT, 453 AM

[56] References Cited

UNITED STATES PATENTS

| | | | |
|---|---|---|---|
| 3,455,836 | 7/1969 | Shultz et al. | 252/182 |
| 3,583,926 | 6/1971 | Zwolinski et al. | 252/182 |
| 3,634,361 | 1/1972 | Shultz et al. | 252/182 |
| 3,640,886 | 2/1972 | Cenker | 252/182 |
| 3,658,762 | 4/1972 | Cobbledick | 252/182 |
| 3,936,483 | 2/1976 | Gemeinhardt | 260/453 AM |
| 3,980,579 | 9/1976 | Syrop et al. | 252/182 |

FOREIGN PATENTS OR APPLICATIONS

| | | | |
|---|---|---|---|
| 1,200,432 | 7/1970 | United Kingdom | 260/453 AM |
| 1,398,975 | 6/1975 | United Kingdom | 260/453 AM |
| 1,417,087 | 12/1975 | United Kingdom | 260/453 AM |

*Primary Examiner*—Richard E. Schafer
*Assistant Examiner*—Irwin Gluck
*Attorney, Agent, or Firm*—Cushman, Darby & Cushman

[57] ABSTRACT

A diphenylmethane diisocyanate composition which comprises diphenylmethane diisocyanate, a diphenylmethane diisocyanate uretonimine group-containing derivative, a reaction product of diphenylmethane diisocyanate and a diol of molecular weight less than 175 and optionally not more than 10% by weight of methylene bridged polyphenyl polyisocyanates of isocyanate functionality higher than two, the composition having an isocyanate functionality of not more than 2.3. Methods of manufacture of such compositions, which compositions are useful for the manufacture of polyurethanes.

10 Claims, No Drawings

DIPHENYLMETHANE DIISOCYANATE COMPOSITIONS

This invention relates to diphenylmethane diisocyanate compositions which comprise diphenylmethane diisocyanate together with diphenylmethane diisocyanate uretonimine group-containing derivatives, reaction products of diphenylmethane diisocyanate and certain diols and optionally methylene bridged polyphenylpolyisocyanates of isocyanate functionality greater than two, the compositions having an average isocyanate functionality of not more than 2.3. The invention also relates to the preparation of such compositions and their use in the manufacture of polyurethanes.

It is well known that diphenylmethane diisocyanate can be used to prepare a wide range of polyurethanes such as surface coatings, foams and elastomers having valuable properties. Refined diphenylmethane diisocyanate, refined by either distillation, crystallisation or a combination of these processes, is normally a solid, melting at about 40° C, and therefore has the disadvantage that it is difficult to handle on the large scale, requiring melting before it can be metered. It also suffers from the defect that on storage in the solid crystalline state slow conversion to uretedione derivatives takes place and as such derivatives are of low solubility, the liquid obtained on melting the diisocyanate is cloudy and difficulty may be experienced in metering the liquid which has first to be filtered.

Various methods of overcoming these disadvantages have been proposed and have generally been aimed at producing diphenylmethane diisocyanate compositions which are liquid at room temperature or have a greatly reduced tendency to crystallise on storage at that temperature. It is also necessary that such compositions, which may be used in the manufacture of semi-rigid or microcellular foams in the form of shoe soles, car bumpers and trim, have a low viscosity and a pre-determined and preferably low isocyanate functionality. Thus various compositions have been made in which a proportion of the isocyanate groups are reacted with hydroxy compounds or are converted to carbodiimide and thus to uretonimine groups.

We have now found that certain diphenylmethane diisocyanate compositions which are of isocyanate functionality not greater than 2.3 and contain both uretonimine and urethane residues are storage-stable liquids of low viscosity eminently suitable for use in the manufacture of polyurethanes particularly semi-rigid and microcellular polyurethane foams.

Thus according to the present invention there is provided a diphenylmethane diisocyanate composition which comprises diphenylmethane diisocyanate, a diphenylmethane diisocyanate uretonimine group-containing derivative, a reaction product of diphenylmethane diisocyanate and a diol of molecular weight less than 175 and optionally not more than 10% by weight of methylene bridged polyphenyl polyisocyanates of isocyanate functionality higher than two, the composition having an isocyanate functionality of not more than 2.3.

Any diphenylmethane diisocyanate may be used in the composition or in the preparation of the uretonimine group-containing derivative and the diol/diphenylmethane diisocyanate reaction product.

Preferably the diphenylmethane diisocyanate has been subjected to at least one purification by distillation or crystallisation. The invention is particularly applicable to diphenylmethane diisocyanates which have been refined by being at least once distilled.

By the term diphenylmethane diisocyanate we mean any isomer or mixture of isomers of diphenylmethane diisocyanate. The commonest isomer at the present time is diphenylmethane-4,4'-diisocyanate and the invention is applicable, for example, to this isomer or to mixtures of this isomer with diphenylmethane-2,4'-diisocyanate optionally containing diphenylmethane-2,2'-diisocyanate. A preferred diphenylmethane diisocyanate to which the invention is applicable is 4,4'-diphenylmethane diisocyanate containing up to 50% of the 2,4'-isomer and optionally up to 5% of the 2,2'-isomer.

A diphenylmethane diisocyanate uretonimine group-containing derivative is a uretonimine derived from diphenylmethane diisocyanate. Such derivatives may be made by converting a proportion of the isocyanate groups in diphenylmethane diisocyanate to carbodiimide groups and then allowing the carbodiimide groups to react with further isocyanate groups to give uretonimine groups.

Thus one of the simplest uretonimine group-containing derivatives would be formed from 3 molecules of diphenylmethane diisocyanate.

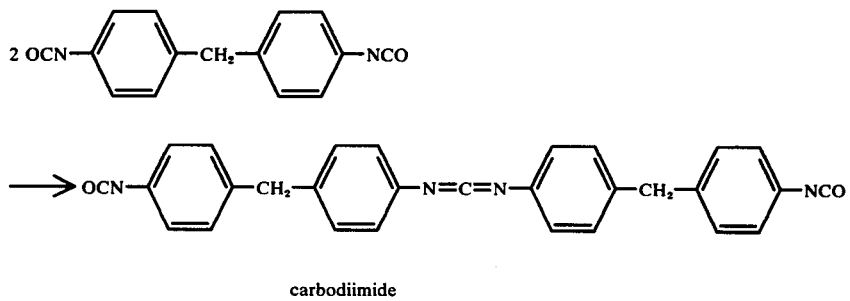

carbodiimide

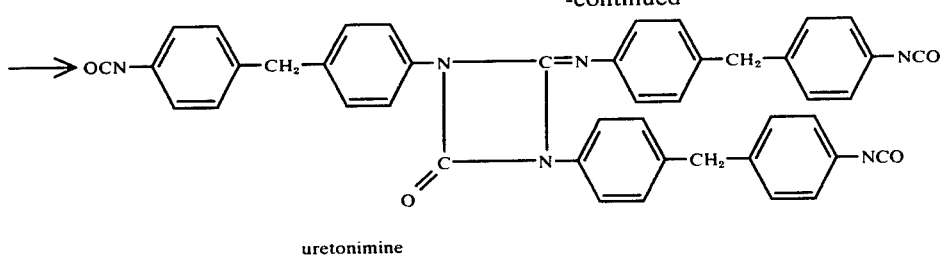

uretonimine

Uretonimine groups are produced by reacting an isocyanate group with a carbodiimide group and may be easily introduced into an isocyanate composition by converting some of the isocyanate groups to carbodiimide groups and then allowing the carbodiimide groups to react with unreacted isocyanate groups to form uretonimine groups. A large variety of phosphorus-containing catalysts have been described for use in the conversion of isocyanate groups to carbodiimide groups.

The conversion of isocyanate groups to carbodiimide groups and the further reaction to give uretonimine groups is known in the art and is for example described in British Pat. No. 1,356,851 and our copending U.S. application Ser. No. 670,155 filed Mar. 25, 1976.

Once carbodiimide groups have been introduced into an isocyanate composition, reaction between carbodiimide groups and isocyanate groups takes place with formation of uretonimine groups. In order to permit this reaction to proceed to near completion it is normally necessary to allow the isocyanate/carbodiimide reaction mixture to stand for a time at room temperature for the uretonimine-forming reaction to take place. Conversion to uretonimine may not go to absolute completion and there sometimes remains in the composition a small amount of carbodiimide which is not converted to uretonimine despite the presence of excess isocyanate groups.

In manufacturing diphenylmethane diisocyanate uretonimine group-containing derivatives for the compositions of this invention it is preferred that about 3.5–35% of the isocyanate groups in diphenylmethane diisocyanate are converted to carbodiimide groups by heating the diisocyanate in the presence of a catalyst and then cooling the mixture, with deactivation of the catalyst if desired or necessary, and then allowing the carbodiimide groups to react further to give the uretonimine derivative. Thus there is obtained diphenylmethane diisocyanate containing a uretonimine group-containing derivative thereof.

The reaction product of a diphenylmethane diisocyanate with a diol having a molecular weight of less than 175 may be any such product made using an appropriate diol or a mixture of diols.

Examples of suitable diols include ethylene glycol, diethylene glycol, triethylene glycol, 2-hydroxyethyl-2'-hydroxypropylether, 1,2-propylene glycol, 1,3-propylene glycol, dipropyl glycol, 1,2-, 1,3- and 1,4-butylene glycols, 1,5-pentane diol, bis-2-hydroxypropyl sulphide, bis-2-hydroxyalkyl carbonates, p-xylylene glycol, 4-hydroxymethyl-2,6-dimethyl phenol and 1,2-, 1,3- and 1,4-dihydroxy benzenes.

Mixtures of diols may be used.

The reaction product may be suitably made by reacting a proportion of the isocyanate groups in a diphenylmethane diisocyanate with the diol and using the product which will contain both diisocyanate/diol reaction product and excess diisocyanate, in the present composition.

Thus, if from 0.05 to 0.35 molar proportions of diol are reacted with 1 molar proportion of diphenylmethane diisocyanate then from 5 to 35% of the isocyanate groups will be reacted. The conditions of reaction of isocyanates and diols are well known and although elevated temperature may be used this is not always necessary.

The fourth and optional component of the composition is no more than 10% by weight of methylene bridged polyphenyl polyisocyanates having an isocyanate functionality greater than two.

Methylene bridged polyphenyl polyisocyanates of isocyanate functionality greater than two are well known and have the general formula:

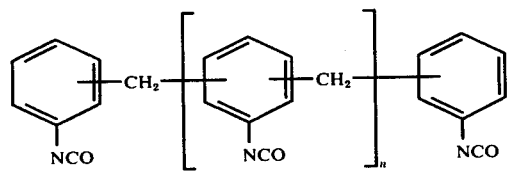

where $n$ is one or more.

They are produced together with diphenylmethane diisocyanates by phosgenation of the condensation product of aniline and formaldehyde produced in the presence of a catalyst such as hydrochloric acid. Mixtures of such isocyanates may conveniently be incorporated into the compositions of the present invention by incorporating the crude phosgenation product from the above-mentioned phosgenation, making due allowance for the diphenylmethane diisocyanate present therein or alternatively by removing some or all of the diisocyanate component from the crude phosgenation product before incorporation. Both diphenylmethane diisocyanate and the diol reaction product have an isocyanate functionality of two and the amount of uretonimine group-containing derivative and the polymethylene polyphenyl polyisocyanates which have a functionality greater than two, present in the composition of the invention must be so adjusted that the average functionality of the composition is not greater than 2.3.

Preferred compositions are those containing 30 to 80% of diphenylmethane diisocyanate;
5 to 25% diphenylmethane diisocyanate uretonimine-containing derivative;
20 to 50% of a reaction product of diphenylmethane diisocyanate and a diol or mixture of diols of M.W. less than 175;
0 to 10% of methylene bridged polyphenyl polyisocyanates of isocyanate functionality higher than two;

the above percentages being by weight and the average functionality of the composition being not more than 2.3.

The compositions of the invention may be made by blending a diphenylmethane diisocyanate/diol reaction product with a diphenylmethane diisocyanate uretonimine group-containing derivative and diphenylmethane diisocyanate and optionally polymethylene polyphenyl polyisocyanates. Each of the above components may themselves contain free diphenylmethane diisocyanate but further diphenylmethane diisocyanate may be incorporated as desired.

In an alternative process the compositions may be made by mixing a solution of a uretonimine group-containing derivative in diphenylmethane diisocyanate with a diol under such conditions that urethane formation but no other reaction takes place for example at a temperature no higher than 85° C, additional diphenylmethane diisocyanate or higher analogues thereof being optionally present or optionally added later.

In one preferred process for manufacturing the compositions of the present invention, diphenylmethane diisocyanate is first treated with a phosphorus-containing catalyst to convert from 10 to 30% of the isocyanate groups to carbodiimide groups which then react with isocyanate groups to give a solution of a uretonimine derivative in the diisocyanate, there is then added from 50 to 150% of diphenylmethane diisocyanate based on the weight of the original diisocyanate and this mixture is then reacted with one or more diols below 85° C in such amount as to give a final composition having an isocyanate group content of from 22 to 30%.

The compositions are of low viscosity, and are storage-stable liquids. The term liquid is used to indicate that the compositions remain liquid at room temperature for long periods of time, sufficient in fact for all practical purposes although on prolonged storage for several years it is possible that some crystallisation will take place. Nevertheless the compositions may for all practical purposes be described as liquids.

The compositions are useful for the manufacture of polyurethanes in particular. By varying the balance of constituents in the composition it is possible to obtain a wide range of physical properties in the composition especially viscosity and a wide range of processing and polymer properties in the derived polyurethanes. The combination considered to be ideal varies with the precise circumstances of manufacture and product properties demanded.

Compositions with from 0.5 to 10% of methylene bridged polyphenyl polyisocyanates of isocyanate functionality higher than two incorporated therein have been found to shorten mould release times, which factor increases the output from a moulded foam operation.

The invention is illustrated by the following Examples in which all parts are parts by weight except where otherwise stated. Where parts by volume are given the relationship between weight and volume is that of the gram to the milliliter.

EXAMPLE 1

To 100 parts of molten distilled diphenylmethane-4,4'-diisocyanate containing 1.5% of the 2,4'-isomer and having an acidity of 69 ppm (calculated as HCl) was added 1-phenyl-3-methyl-2-phospholene-1-oxide in an amount of 5 parts per million of isocyanate (i.e. 0.5 parts by volume of a 1% w/v solution in perchloroethylene) and epichlorohydrin, 0.35 parts, corresponding to two moles per mole of acidity present.

The solution was stirred for 2 hours at 120° C and then cooled to 50° C. The isocyanate content of this partially uretonimine modified diisocyanate was 27% (determined by the di-n-butylamine method).

A further quantity of the diisocyanate starting material was added to give a final isocyanate content of 29%. (Sample A).

To 250 parts of Sample A was added 250 parts of the distilled diphenylmethane diisocyanate used as starting material and the mixture maintained at 80° C whilst adding 26.8 parts of dipropylene glycol over 30 minutes, after the addition the solution was stirred for 1 hour at 80° C and then cooled to room temperature to give as product a pale straw-coloured liquid of viscosity 1.30 poise and isocyanate group content 26.2% which was stable to storage at 20° C.

EXAMPLE 2

To 250 parts of Sample A from Example 1 was added with stirring at 80° C, 26.8 parts of dipropylene glycol over 30 minutes. After maintaining this temperature for one hour a further 250 parts of the original diphenylmethane diisocyanate starting material from Example 1 was added and the whole cooled to room temperature to give as final product a pale straw-coloured liquid of isocyanate group content 26.8% and viscosity 1.36 poise.

EXAMPLE 3

To 250 parts of diphenylmethane-4,4'-diisocyanate as used in Example 1, maintained at 80° C, was added 26.8 parts of dipropylene glycol during 30 minutes and the reaction mixture kept at 80° C for 1 hour. The product was blended with 250 parts of the uretonimine modified diisocyanate (Sample 1) of Example 1 to give a final composition of isocyanate group content 26.6% and viscosity 1.25 poise, stable at 10° C for 12 days.

EXAMPLE 4

To 750 parts of 4,4'-diisocyanatodiphenylmethane containing 1.2% of the 2,4'-isomer and having an acidity of 41 ppm calculated as hydrochloric acid was added 3.75 parts of a 0.1% solution of 1-phenyl-3-methylphospholene-1-oxide and 0.156 parts by volume of epichlorohydrin. The solution was held at 115° C for 200 minutes, cooled to 80° C and after an hour the product was analysed and found to contain 27% of isocyanato groups. The calculated amount of the pure diisocyanate was added to adjust the isocyanate group content to 31.25% then 0.037 parts by volume of thionyl chloride and 0.112 parts by volume of benzoyl chloride added. A diol blend (95 parts) was added during 90 minutes at 80° C. After a further hour at 80° C the product was cooled and was found to be of isocyanate content 25.6% and viscosity 1.88 poise. The final composition was a clear pale straw coloured liquid having acidity of 18 ppm calculated as hydrogen chloride. After heating at 80° C for four days it had an isocyanate content of 24.5% showing it to be relatively storage stable. It remained liquid on storage at room temperature.

The diol blend used comprised diethylene glycol, 1,2-propylene glycol and 1,3-butylene glycol in the ratio 7.15 : 5.12 : 6.05.

EXAMPLE 5

Example 4 was repeated using 250 parts of the same diisocyanate and correspondingly reduced weights of catalyst and epichlorohydrin. Reaction was carried out in the same way to provide a uretonimium modified diisocyanate of isocyanate value 27.7%.

Thionyl chloride, 0.012 parts by volume, and benzoyl chloride, 0.037 parts by volume, were added, then 379 parts of the original diisocyanate blended into the mixture to raise the isocyanate content to 30.9%. Mixed diols (28.4 parts) as used in Example 4 were added during one hour at 80° C, then the isocyanate content adjusted to 25.8% by adding a further 89 parts of the original diisocyanate.

Analysis showed the product to be of viscosity 1.67 poise and acid content 25 ppm as hydrogen chloride. On heating at 80° C a sample fell in isocyanate content to 24.7% showing the product to be storage stable.

EXAMPLE 6

The experiment of Example 4 was repeated using 250 parts of the same diisocyanate, 0.052 parts by volume of epichlorohydrin and 1.25 parts of a 0.1% solution of 1-phenyl-3-methylphospholene oxide. After 3 hours at 115° C the isocyanate content fell to 27%. After holding for a further hour at 80° C, the strength fell to 26.4%. The product was cooled to 50° C and thionyl chloride, 0.012 parts by volume, and benzoyl chloride, 0.036 parts by volume, added. The isocyanate content was adjusted to 30.8% by adding 518 parts of the original diisocyanate then the diol blend of Example 4 (34.7 parts) was added at 80° C over 1 hour. The isocyanate content of the clear water-white liquid product was 25.25%, its acidity 24 ppm of hydrogen chloride, and viscosity 2.58 poise.

EXAMPLE 7

100 Parts of the product of Example 4 having an average functionality of 2.15 was blended with 20 parts of a mixture of methylene bridged polyphenyl polyisocyanates made by phosgenating the polyamines obtained by condensing aniline and formaldehyde in the molar ratio 2.05/1 in the presence of HCl, the mixed polyisocyanates having an isocyanate functionality of 2.66, to give a darker coloured clear liquid of average functionality 2.24. This composition was very resistant to crystallisation at low temperatures.

EXAMPLE 8

To 100 parts of the diisocyanate/dipropylene glycol reaction product of Example 3 was added 25 parts of the uretonimine modified MDI of isocyanate content 29% (Sample A) described in Example 1 and 50 parts of a mixture of methylene bridged polyphenyl polyisocyanates made by phosgenating the polyamines obtained by condensing aniline and formaldehyde in the molar ratio 1.85/1 in the presence of HCl.

There was obtained a liquid composition of average functionality 2.27 which was of good storage stability at low temperatures.

It is to be noted in both Examples 7 and 8 that the mixtures of methylene bridged polyphenyl polyisocyanates contained at least 50% of diphenylmethane diisocyanates and that the final compositions contained less than 10% by weight of methylene bridged polyphenyl polyisocyanates of isocyanate functionality greater than two.

EXAMPLE 9

A polyurethane foam was made from the composition of Example 4 as follows:

80 parts of an ethylene oxide tipped polypropylene glycol M.W. 3750
20 parts of a 14% ethylene oxide tipped oxypropylated glycerol M.W. 5300
15.3 parts butane diol
1.5 parts ethylene glycol
1 part DABCO
0.03 parts dibutyltin dilaurate The above components were blended together and there was added thereto with efficient mixing, 74.4 parts of the composition of Example 4.

Rapid reaction took place with formation of a high density foamed elastomer of a quality suitable for use for example as a shoe sole or as a car bumper.

Similar foams were readily made from the compositions described in the remainder of Examples 1 to 8.

EXAMPLE 10

The preparation of Example 4 was repeated except that the uretonimine modified diphenylmethane diisocyanate concentrate was blended with a crude diphenylmethane diisocyanate composition containing 20.5% of 2,4'-diisocyanatodiphenylmethane and 400 ppm acidity prior to adding the diol blend. The final composition was stable indefinitely at 10° C.

EXAMPLE 11

735 Parts of 4,4'-diisocyanatodiphenylmethane was blended with 15 parts of the uretonimine modified diisocyanate described in Example 1 (Sample A). To this blend was added 0.150 parts by volume of benzoyl chloride followed by 67.7 parts of a diol mixture. The diol mixture was added over a period of 30 minutes and the addition temperature was maintained at 80° C. The diol mixture comprised diethylene glycol, 1,2-propylene glycol and 1,3-butylene glycol in the ratio 7.5 : 5.12 : 6.05. After a further hour at 80° C the product was cooled and was found to be of isocyanate content 23.0% and viscosity 18.7 poise at 25° C. The product was a clear pale straw-coloured liquid.

EXAMPLE 12

675 Parts of 4,4'-diisocyanatodiphenylmethane was blended with 75 parts of the uretonimine modified diisocyanate described in Example 1 (Sample A). To this blend was added 0.150 parts by volume of benzoyl chloride followed by 66 parts of the diol mixture described in the previous example. The diol mixture was added over a period of 30 minutes and the addition temperature was maintained at 80° C. After a further hour at 80° C the product was cooled and was found to be of isocyanate content 23.10% and viscosity 16.9 poise at 25° C. The product was a clear pale straw-coloured liquid.

EXAMPLE 13 a. Diphenylmethane-4,4'-diisocyanate (100 parts) was mixed with 1-phenyl-3-methylphospholene-1-oxide (5 ppm of diisocyanate) and the mixture heated at 120° C until the isocyanate group content fell to 24.9%. The product was mixed with an equal weight of the original diisocyanate to give a relatively dilute solution of uretonimine-modified diisocyanate of isocyanate group content 28.9%.

b. A diisocyanate/diol reaction product was prepared by adding 9.16 parts of an equimolar blend of diethylene glycol, 1,2-propylene glycol and 1,3-butylene glycol to 100 parts of diphenylmethane-4,4'-diisocyanate and heating at 80° C for 1 hour. Final isocyanate group content 23.1%.

Two compositions exemplifying the present invention were made by blending together (a) and (b) in the proportions 1:1 and 1:3 respectively. The first has viscosity 2.1 poise and the second viscosity 7 poise at 25° C.

EXAMPLE 14

100 Parts diphenylmethane-4,4'-diisocyanate was reacted with 30 parts of polyethylene glycol (M.W.300) by the method of Example 13(b). Final isocyanate group content 19.4%.

Equal parts of the above and of (a) of Example 13 were mixed to give a composition which was a mobile liquid of isocyanate group content 22.6% which was highly resistant to crystallisation at room temperature.

I claim:

1. A diphenylmethane diisocyanate composition which comprises diphenylmethane diisocyanate, a diphenylmethane diisocyanate uretonimine group-containing derivative, a reaction product of diphenylmethane diisocyanate and a diol of molecular weight less than 175 and not more than 10% by weight of methylene bridged polyphenyl polyisocyanates of isocyanate functionality higher than two, the composition having an isocyanate functionality of not more than 2.3.

2. A diphenylmethane diisocyanate composition as claimed in claim 1 wherein the diphenylmethane diisocyanate used in the composition and in the preparation of the uretonimine group-containing derivative and the diol/diphenylmethane diisocyanate reaction product has been subjected to at least one purification by distillation or crystallisation.

3. A diphenylmethane diisocyanate composition as claimed in claim 2 wherein the diphenylmethane diisocyanate has been at least once distilled.

4. A diphenylmethane diisocyanate composition as claimed in claim 2 wherein the diphenylmethane diisocyanate is diphenylmethane-4,4'-diisocyanate containing up to 50% of the 2,4'-isomer and up to 5% of the 2,2'-isomer thereof.

5. A diphenylmethane diisocyanate composition as claimed in claim 1 wherein the uretonimine group-containing derivative is made by converting from 3.5 to 35% of the isocyanate groups in diphenylmethane diisocyanate to carbodiimide groups by heating the diisocyanate in the presence of a catalyst, cooling the mixture, deactivating the catalyst if desired and then allowing the carbodiimide groups to react further to give the uretonimine derivative.

6. A diphenylmethane diisocyanate composition as claimed in claim 1 wherein the reaction product of the diol and diphenylmethane diisocyanate is the reaction product of 0.05 to 0.35 molar proportions of diol with 1 molar proportion of diphenylmethane diisocyanate.

7. A diphenylmethane diisocyanate composition as claimed in claim 1 having the composition:

30 to 80% of diphenylmethane diisocyanate,
5 to 25% of diphenylmethane diisocyanate uretonimine group-containing derivative,
20 to 50% of a reaction product of diphenylmethane diisocyanate and a diol or mixture of diols of M.W. less than 175 and
0 to 10% of methylene bridged polyphenyl polyisocyanates of isocyanate functionality higher than two, the above percentages being by weight and the average isocyanate functionality of the composition being not more than 2.3.

8. A process for the manufacture of a diphenylmethane diisocyanate composition as claimed in claim 1 which comprises blending a diphenylmethane diisocyanate diol reaction product with a diphenylmethane diisocyanate uretonimine group-containing derivative and diphenylmethane diisocyanate and optionally methylene bridged polyphenyl polyisocyanates of isocyanate functionality greater than two.

9. A process for the manufacture of a diphenylmethane diisocyanate composition as claimed in claim 1 which comprises mixing a solution of a uretonimine group-containing derivative of diphenylmethane diisocyanate in diphenylmethane diisocyanate with a diol or mixture of diols under such conditions that urethane formation but no other reaction takes place.

10. A process for the manufacture of a diphenylmethane diisocyanate composition as claimed in claim 1 wherein diphenylmethane diisocyanate is first treated with a phosphorus-containing catalyst to convert from 10 to 30% of the isocyanate groups to carbodiimide groups which then react with isocyanate groups to give a solution of the uretonimine group-containing derivative in the diisocyanate, there is then added from 50 to 150% of diphenylmethane diisocyanate based on the weight of the original diisocyanate and this mixture is then reacted with one or more diols below 85° C in such amount as to give a final composition having an isocyanate group content of from 22 to 30% and optionally up to 10% by weight of methylene bridged polyphenyl polyisocyanates having an isocyanate functionality greater than two are added to the composition.

* * * * *